(12) United States Patent
Kreh et al.

(10) Patent No.: US 7,224,446 B2
(45) Date of Patent: May 29, 2007

(54) APPARATUS, METHOD, AND COMPUTER PROGRAM FOR WAFER INSPECTION

(75) Inventors: Albert Kreh, Solms (DE); Henning Backhauss, Wetzlar (DE)

(73) Assignee: Vistec Semiconductor Systems GmbH, Wetzlar (DE)

(*) Notice: Subject to any disclaimer, the term of this patent is extended or adjusted under 35 U.S.C. 154(b) by 317 days.

(21) Appl. No.: 10/880,122

(22) Filed: Jun. 30, 2004

(65) Prior Publication Data
US 2005/0002021 A1    Jan. 6, 2005

(30) Foreign Application Priority Data
Jul. 3, 2003    (DE) .................. 103 30 003

(51) Int. Cl.
*G01N 21/00* (2006.01)
(52) U.S. Cl. .................. 356/237.4; 356/237.5
(58) Field of Classification Search .. 356/237.1–237.5; 382/144–145
See application file for complete search history.

(56) References Cited

U.S. PATENT DOCUMENTS

| | | | |
|---|---|---|---|
| 5,365,084 A | | 11/1994 | Cochran et al. |
| 6,556,291 B2* | | 4/2003 | Yonezawa ............ 356/237.2 |
| 2001/0012393 A1* | | 8/2001 | Yonezawa ............... 382/145 |
| 2002/0005946 A1 | | 1/2002 | Oomori et al. |
| 2002/0101200 A1* | | 8/2002 | Dowling et al. ........... 315/292 |
| 2003/0011910 A1 | | 1/2003 | Weiss |
| 2003/0107887 A1 | | 6/2003 | Eberl |
| 2006/0203213 A1* | | 9/2006 | Kobayashi ................ 355/1 |

FOREIGN PATENT DOCUMENTS

| | | |
|---|---|---|
| DE | 41 23 916 C2 | 1/1992 |
| DE | 43 16 624 A1 | 12/1994 |
| DE | 100 31 303 A1 | 1/2002 |
| DE | 101 32 360 C1 | 11/2002 |
| EP | 1 107 012 A1 | 6/2001 |
| JP | 10-144123 A | 5/1998 |
| JP | 10-318881 A | 12/1998 |
| WO | WO 02/18913 A2 | 3/2002 |

* cited by examiner

*Primary Examiner*—Hoa Q. Pham
(74) *Attorney, Agent, or Firm*—Foley & Lardner LLP (57) ABSTRACT

The invention concerns an apparatus for inspection of a wafer, encompassing at least one illumination device in order to radiate an illuminating light beam onto a surface of the wafer, and an image capture device in order to capture an image of an illuminated region on the surface of the wafer in a plurality of spectral regions, a color modification device being provided in order to modify the color spectrum of the illuminating light beam or of the reflected light beam. The wafer inspection apparatus is characterized in that the color modification device is designed in such a way that the color spectrum of the illuminating light beam, or that of the image that is acquired of the surface of the wafer, is adaptable to the spectral sensitivity of the image capture device.

24 Claims, 5 Drawing Sheets

APPARATUS, METHOD, AND COMPUTER PROGRAM FOR WAFER INSPECTION

CROSS REFERENCE TO RELATED APPLICATIONS

This application claims priority of the German patent application 103 30 003.1 which is incorporated by reference herein.

FIELD OF THE INVENTION

The present invention concerns an apparatus, a method, and a computer program for inspection of a wafer, in particular for the detection of macrodefects on the surface of a wafer.

BACKGROUND OF THE INVENTION

Apparatuses for the detection of macrodefects on the surface of wafers are used to improve quality and efficiency in the production of integrated circuits, so that wafers found to be defective can be discarded or can be reprocessed until the quality of a wafer that has just been inspected is satisfactory.

Optical wafer inspection apparatuses are known that encompass an illumination device for radiating an illuminating light beam onto a surface of the wafer, and an image capture device for capturing an image of an illuminated region on the surface of the wafer in a plurality of spectral regions, i.e. in spectrally resolved fashion. Problems can occur in the further processing of the color image signals captured by the image capture device if the color image channels of the image capture device are modulated non-uniformly; this can result in a relatively low signal-to-noise ratio, or saturation, in individual color image channels.

DE 101 32 360 C1 discloses an apparatus for color-neutral brightness adjustment in the illumination beam path of a microscope. The apparatus is based on the recognition that in microscopes operated with an incandescent lamp similar to a black body, upon a reduction in the power level delivered to the lamp, the color temperature of the color spectrum emitted by the incandescent lamp is shifted from the blue spectral region to the red spectral region. To compensate for the red shift, there is provided in the illumination beam path a variable optical filter whose transmittance for red light changes over the filter surface. Displacement of the filter in the illumination beam path brings about a blue shift which compensates for the red shift caused by the diminution in electrical power.

DE 100 31 303 A1 discloses an illumination apparatus having LEDs. Degeneration of the LED material causes a change over time in the intensity and wavelength of the emitted LED light. To achieve consistent illumination properties, a control system is provided so that a predefined color temperature and intensity can be maintained for the LEDs.

SUMMARY OF THE INVENTION

It is the object of the present invention to make available an apparatus with which macrodefects on the surface of a wafer can be detected even more reliably.

This object is achieved by an apparatus for inspection of a wafer comprising: at least one illumination device that radiates an illuminating light beam onto a surface of the wafer, an image capture device that has a predefined spectral sensitivity and captures an image of an illuminated region on the surface of the wafer in a plurality of spectral regions, and a color modification device in order to modify the color spectrum of the illuminating light beam or that of the image that is acquired of the surface of the wafer, wherein the color modification device is designed in such a way that the color spectrum of the illuminating light beam, or that of the image that is acquired of the surface of the wafer, is adaptable to the spectral sensitivity of the image capture device.

It is the object of the present invention to make available a method, with which macrodefects on the surface of a wafer can be detected even more reliably.

The object is achieved by a method comprising the steps of:
radiating an illuminating light beam of at least one illumination device onto a surface of the wafer,
capturing an image of an illuminated region on the surface of the wafer by an image capture device, wherein the image capture device has a predefined spectral sensitivity in a plurality of spectral regions
modifying the color spectrum of the illuminating light beam, or that of the image that is acquired of the surface of the wafer, and
carrying out the modification such that the color spectrum of the illuminating light beam, or that of the image that is acquired of the surface of the wafer, is adapted to the spectral sensitivity of the image capture device.

It is the object of the present invention to make available a computer program with which macrodefects on the surface of a wafer can be detected even more reliably.

The above object is achieved by a computer program that carries out the following method steps:
radiating an illuminating light beam of at least one illumination device onto a surface of the wafer,
capturing an image of an illuminated region on the surface of the wafer by an image capture device, wherein the image capture device has a predefined
spectral sensitivity in a plurality of spectral regions,
modifying the color spectrum of the illuminating light beam, or that of the image that is acquired of the surface of the wafer, and
carrying out the modification such that the color spectrum of the illuminating light beam, or that of the image that is acquired of the surface of the wafer, is adapted to the spectral sensitivity of the image capture device.

According to the present invention, an apparatus for inspection of a wafer is made available, having at least one illumination device that radiates an illuminating light beam onto a surface of the wafer, and an image capture device that has a predefined spectral sensitivity and captures an image of an illuminated region on the surface of the wafer in a plurality of spectral regions, a color modification device being provided in order to modify the color spectrum of the illuminating light beam or that of the image that is acquired of the surface of the wafer. The apparatus is characterized, according to the present invention, in that the color modification device is designed in such a way that the color spectrum of the illuminating light beam, or that of the image that is acquired of the surface of the wafer, is adaptable to the spectral sensitivity of the image capture device.

Image capture devices, for example color CCD cameras, usually have differing spectral sensitivities in the spectral regions used for image capture, for example in the red, green, and blue spectral regions. In addition, the illumination device also exhibits a certain color spectrum, for example that of a thermal radiator having a predefined color temperature. This can result in differing intensities for the individual color image signals of the image capture device.

The intensities of the individual color image signals of the image capture device can in fact differ considerably from one another.

According to the present invention, this problem is resolved by the fact that a color modification device acts in controlled fashion on the illuminating light beam, or on light from the surface region of the wafer captured by the image capture device, in order to adapt the respective color spectrum to the spectral sensitivity of the image capture device. For that purpose, the intensity of the illuminating light beam, or of light from the surface region of the wafer captured by the image capture device, is attenuated in controlled fashion in individual spectral regions, so that a more uniform modulation of the color image channels of the image capture device can be achieved.

Preferably, the intensity of a color image signal of the image capture device in one spectral region is modified by modifying the color spectrum of the illuminating light beam, or that of the image of the surface of the wafer acquired by the image capture device, relative to the intensity of a different color image signal of the image capture device in a different spectral region. This relative change can be achieved by selective attenuation of the illuminating light beam in individual spectral regions, or of light that derives from the surface region of the wafer captured by the image capture device.

It is advantageous that by adaptation of the color spectrum of the illuminating light beam, or that of the image of the surface of the wafer captured by the image capture device, a more uniform modulation of the color image channels of the image capture device can be achieved. Preferably, for this purpose, the intensity of the illuminating light beam, or that of the image of the surface of the wafer acquired by the image capture device, is increased with the aid of a color modification device, in at least one spectral region in which the color image signal captured by the image capture device has a relatively low amplitude, relative to the corresponding intensity in a different spectral region, so that a sufficient amplitude of the captured color image signal is achieved. Even if the specific reason for a nonuniform modulation of the color image channels is not exactly known, according to the present invention a more uniform modulation of the color image channels can be achieved simply by testing, for example on a reference wafer.

It is further advantageous that a higher detection sensitivity can also be achieved as a result of the more uniform modulation of the color image channels. In particular, according to the present invention signals having a higher signal-to-noise ratio can be achieved, offering advantages in the context of image capture and subsequent image evaluation.

According to the present invention, the color modification device acts selectively on one or more spectral regions of the illuminating light beam, or of the image of the surface of the wafer captured by the image capture device, in order selectively to modify the intensity in the respective spectral region and thus to modify the color spectrum. This modification of the color spectrum can be brought about by way of diffractive or refractive effects, for example using diffraction gratings, diffraction grating arrangements, prisms, or prism arrangements. In very particularly preferred fashion according to the present invention, the intensity of the illuminating light beam or of the reflected light beam is selectively attenuated in at least one spectral region. An attenuation of this kind can likewise be achieved, in principle, using the aforesaid diffractive or refractive effects. In very particular preferred fashion according to the present invention, however, a selective spectral filtration of the illuminating light beam, or of the image of the surface of the wafer captured by the image capture device, is brought about using a color filter, for example a colored glass filter, an interference filter, or a dichroic filter.

By appropriate selection of the spectral properties of the color modification device, the intensities of the color image signals captured by the image capture device can be modified almost arbitrarily relative to one another. Preferably, however, an adaptation to the spectral sensitivity of the image capture device is implemented in such a way that a maximally uniform modulation of the color image channels of the image capture device is attained. For that purpose, the color spectrum of the illuminating light beam, or that of the image of the surface of the wafer captured by the image capture device, can be modified, for example, in such a way that a ratio of the intensity of one color image signal to an intensity of a different color signal of the image capture device is increased by a factor of at least approximately 1.5, preferably at least approximately 2.0, and even more preferably at least approximately 3.0. The aforesaid parameter ranges have proven particularly useful for the detection of macrodefects on the surface of silicon wafers.

Especially when thermal radiators are used as illumination devices, it has been found that the color image signals of the image capture device in the red spectral region are relatively low as compared with those in the blue spectral region. It is therefore particularly useful according to the present invention to increase the intensity of the color image signal in the red spectral region by modifying the color spectrum of the illuminating light beam, or that of the image of the surface of the wafer captured by the image capture device, relative to the intensity of the color image signal in the blue spectral region. This is done, according to the present invention, by attenuating the illuminating light beam, or the image of the surface of the wafer captured by the image capture device, in the blue spectral region. Because the illumination device exhibits a spectral distribution defined by the color temperature, the intensity of the color image signal in the red or blue spectral region is thus also automatically modified relative to the intensity of the color image signal in the green spectral region. The color modification device can, of course, also act on other spectral regions of the illuminating light beam, or of the image of the surface of the wafer captured by the image capture device.

In principle, according to the present invention, the surface of the wafer can be inspected in any desired spectral regions, for example in the far infrared (FIR) spectral region and/or in the near infrared (NIR) spectral region and/or in the visible spectral region at wavelengths between approximately 400 and 800 nm and/or in the ultraviolet spectral region. The prerequisite is always that image sensors of suitable quality and spectral sensitivity be available for image capture, and that the wavelengths used be suitable for the detection of macrodefects. It is very particularly preferred to use wavelengths in the visible spectral region, since commercial CCD cameras can thus be used as the image capture device.

According to a first embodiment, thermal radiators are used as the light source of the illumination device. In this embodiment, the color spectrum of the illuminating light beam can also be modified by appropriate selection of a dichroic coating in a reflector housing of the light source.

In very particularly preferred fashion, the illumination device encompasses a xenon flash lamp as the thermal radiator. For the inspection of wafers, it is preferable to use in this context a color temperature orange (CTO) filter which changes the color temperature of the illuminating light beam, for example, from approximately 15,000 K to approximately 5600 K.

It may in principle be sufficient if the transmittance of the color filter being used is defined once, so that for adaptation to the wafers being examined and their surfaces, the color spectrum of the illuminating light beam, or that of the image of the surface of the wafer captured by the image capture device, is adapted to the spectral sensitivity of the image capture device being used. For example, the transmittance can be adapted in advance using a reference wafer having preferred surface properties.

According to a further embodiment, the transmittance of the color filter can also be variable, for example continuously modifiable; this makes the wafer inspection apparatus even more versatile, since the detection sensitivity can still be adapted even during individual measurements or measurement series. For that purpose, the transmittance of the color filter can be varied, for example, spatially, and a desired transmittance can be defined by spatial displacement of the color filter in the respective beam path of the illuminating light beam or of the image of the surface of the wafer captured by the image capture device.

According to a further embodiment, the light source, for example a thermal radiator, is not arranged directly in the illumination device, but rather the light of the light source is coupled into a light guide or a light guide bundle and conveyed to the illumination device in order to be radiated thereby. With this embodiment, a filter serving as a color modification device, for example a color filter, an interference filter, or a dichroic filter, is preferably arranged in the beam path between the light source and the end face of the light guide or guides. The filter and the light guide or guides are preferably retained together.

According to a further embodiment, instead of one thermal radiator as the colored light source of the illumination device, at least three colored light sources are used that each radiate illuminating light beams in different spectral regions, for example in the three primary colors red, green, and blue. The colored light sources can, of course, also emit in other spectral regions, for example in the far infrared (FIR) spectral region and/or in the near infrared (NIR) spectral region and/or in the visible spectral region at wavelengths between approximately 400 nm and approximately 800 nm and/or in the ultraviolet spectral region. The colored light sources are preferably light sources that each emit substantially at only one wavelength. In particularly preferred fashion, LEDs or laser diodes are used that each emit at different wavelengths.

With this embodiment, the intensity of the respective illuminating light beam can be varied in advantageously simple fashion by modifying the respective driver current strength, so that the color spectrum of the illuminating light beam, and thus also that of the image of the surface of the wafer captured by the image capture device, can be adapted to the spectral sensitivity of the image capture device. The overall result is that a more uniform modulation of the color image channels of the image capture device can be achieved. With this embodiment, a shared control unit can be provided for modifying the driver current strengths.

The control unit is preferably connected via a data connection to the data readout device that reads out the image data of the image capture device. The data readout device, for example a computer on which the color image signals read out from the image capture device can be displayed or indicated, can be used to adapt the respective driver current strengths of the colored light sources in such a way that a more uniform modulation of the color image channels can be achieved. It is thus also possible, in simple fashion, to implement an open or closed control loop in order to adapt the respective driver current strengths of the colored light sources automatically, so that a more uniform modulation of the color image channels can be achieved.

A CCD camera, which comprises a CCD image sensor or a plurality of CCD image sensors that are each associated with a spectral color that is to be detected, is preferably used as the image capture device.

According to a further aspect of the present invention, a method for inspection of a wafer is also made available, in which at least one illumination device radiates an illuminating light beam onto a surface of the wafer, and an image capture device that has a predefined spectral sensitivity captures an image of an illuminated region on the surface of the wafer in a plurality of spectral regions, the color spectrum of the illuminating light beam, or that of the image of the surface of the wafer acquired by the image capture device, being modified in such a way that the color spectrum of the illuminating light beam, or that of the image that is acquired of the surface of the wafer, is adapted to the spectral sensitivity of the image capture device.

With this method, the intensity of a color image signal of the image capture device in one spectral region can be increased relative to the intensity of a different color image signal of the image capture device in a different spectral region.

The method is preferably carried out automatically in the manner described in conjunction with the corresponding apparatus, for which purpose, according to the present invention, a suitable control program in the form of software or a software program is also made available.

BRIEF DESCRIPTION OF THE DRAWINGS

The invention will be described below by way of example and with reference to the appended drawings, from which further features, objects, and advantages of the present invention are apparent. In the drawings.

In the Figures, identical reference characters designate identical or substantially identically functioning elements or functional groups.

DETAILED DESCRIPTION OF THE INVENTION

Figure 1:
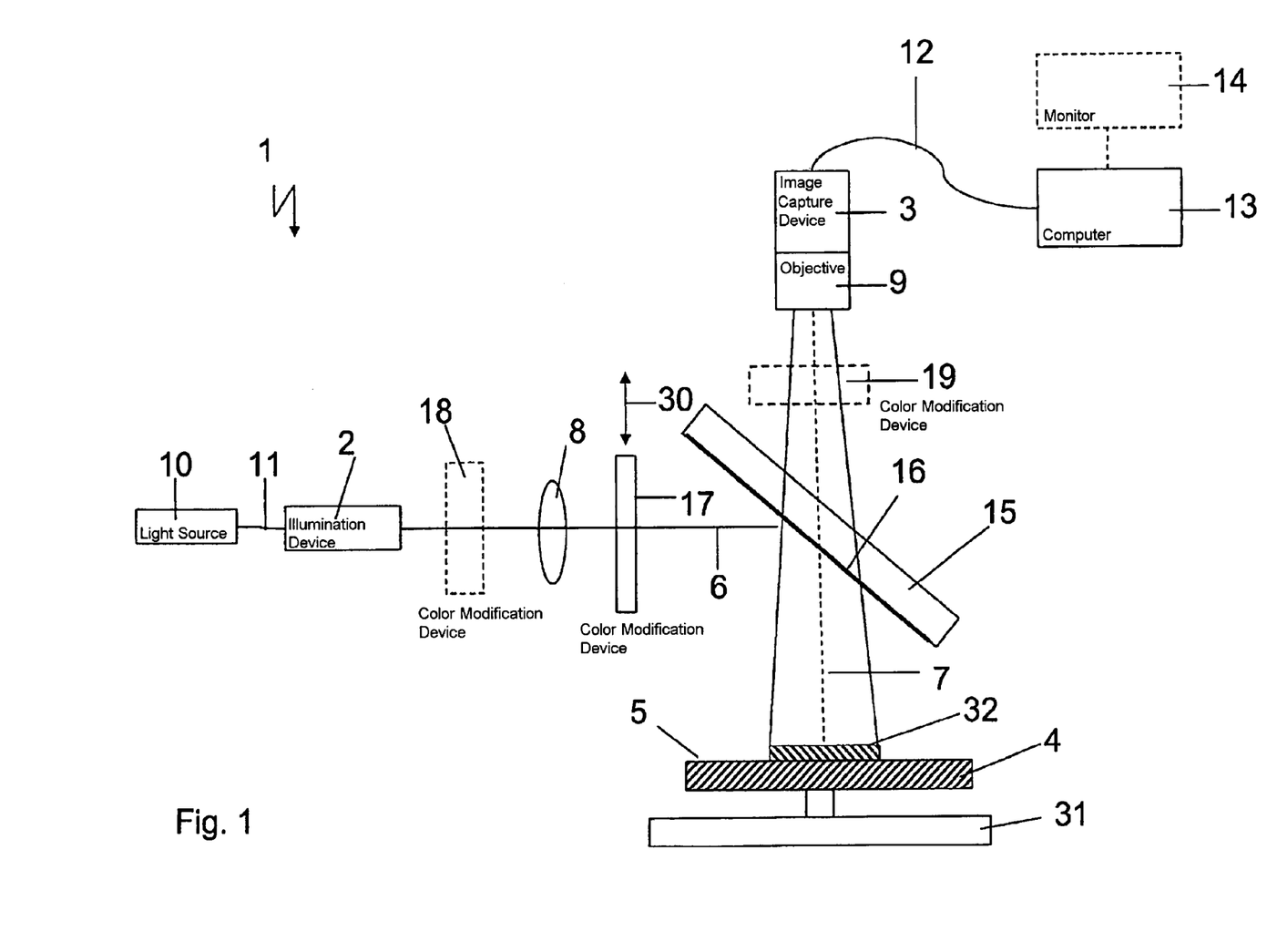
FIG. 1 shows a first embodiment of a wafer inspection apparatus according to the present invention, with detection in a bright-field arrangement.

FIG. 1 shows a first embodiment of a wafer inspection apparatus according to the present invention. Wafer inspection apparatus 1 encompasses an illumination device 2 and a CCD camera 3 serving as image capture device. Illumination device 2 radiates, along illumination axis 6, an illuminating light beam that is reflected by semitransparent mirror 15 onto surface 5 of wafer 4. The illuminating light beam can illuminate the entire surface 5 or a portion thereof. The light reflected from surface 5 of wafer 4 in illuminated region 32 is reflected along imaging axis 7 into CCD camera 3, passing through semitransparent mirror 15. An imaging optical system associated with CCD camera 3, for example an objectives, 9, images the reflected light beam onto CCD camera 3. CCD camera 3 generates a color image of illuminated region 32 on surface 5 of wafer 4. Camera 3 is connected via data line 12 to a frame grabber (not depicted) serving as a data readout device, and to a computer 13 that reads out the color image signals of CCD camera 3. The color image signals that are read out are displayed on a monitor 14 and further evaluated, optionally after appropriate image processing by means of software.

As FIG. 1 shows, illumination device 2 has associated with it a light source 10 whose light is coupled in via light guide bundle 11. The illuminating light beam radiated by illumination device 2 is imaged with the aid of imaging optical system 8, for example a lens or a lens system, onto surface 5 of wafer 4.

In the arrangement shown in FIG. 1, the illuminating light reflected from surface 5 of wafer 4 is reflected directly into CCD camera 3. Wafer inspection apparatus 1 thus, according to FIG. 1, detects macrodefects on surface 5 of wafer 4 in a bright-field arrangement.

Illumination device 2 radiates light in a visible spectral region. The reflected light is detected by CCD camera 3 in spectrally resolved fashion. In each spectral region, the CCD camera furnishes integral values after image acquisition.

CCD camera 3 captures the reflected light in three or four different spectral regions. CCD cameras having three spectral regions generally use RGB primary valences to capture the signals. In CCD cameras having four different filters, complementary-color filters are preferred. These filters can be arranged on the CCD matrix in different ways. Matrices having complementary-color filters are usually designed in such a way that it is very easy to calculate therefrom a YCrCb signal that is required for generation of a TV-compatible image. RGB matrices, on the other hand, are intended for signal processing and display on a computer monitor.

Spectral resolution can be implemented in CCD camera 3, in known fashion, by positional signal separation, by time-based signal separation, or by optical signal separation. In one-chip cameras, a CCD sensor (not depicted) of CCD camera 3 has in front of it an RGB filter mask that permits the radiation of only certain wavelengths to the CCD sensor. The most common filter type is a mosaic filter in which four adjacent CCD sensors generate a color pixel using a spatially associated filter arrangement. It is preferable according to the present invention to use a three-chip camera in which, instead of a color filter in front of a CCD sensor, a system of prisms is used for beam splitting and spatial beam separation. The incident light radiation is spectrally subdivided by the prisms, and the three resulting spectrally separated light beams are then imaged onto three spatially separated CCD sensors of CCD camera 3.

The CCD sensors of CCD camera 3 capture color image signals in a respective spectral region. The intensity of the captured color image signals can be different, for example for one of the following reasons: illumination device 2 has a color spectrum that is not adapted to the spectral sensitivity of CCD camera 3 or of the CCD sensors; the spectral sensitivity of the CCD sensors may be different in the spectral regions; the reflectivity of wafer 4 to be inspected may be different in the spectral regions; or optical elements in the beam path of the incident illuminating light beam or the reflected light beam may have a spectrally differing transmittance or reflectivity, which influences the spectral distribution of the detected light.

Because of the differing intensities of the color image signals, the color image channels of CCD camera 3 are modulated differently, resulting in saturation or differing signal-to-noise ratios in the various color image channels. A low signal-to-noise ratio can negatively affect the accuracy of image capture and image evaluation.

To resolve this problem, wafer inspection apparatus 1 according to the present invention encompasses a color filter 17, serving as color modification device, that is arranged either in the beam path of the illuminating light beam from CCD camera 3 to surface 5 of wafer 4, or in the beam path of the light beam reflected, scattered, or diffracted from surface 5 of wafer 4 to CCD camera 3. The various possible positions of color filter 17 are indicated in FIG. 1 by positions 18 and 19 drawn with dashed lines.

Alternatively or additionally, the surface of semitransparent mirror 15 can also have a dichroic coating 16 serving as color modification device, so that the illuminating light beam, and/or the light reflected, scattered, or refracted from surface 5 of wafer 4, is reflected or transmitted in spectrally different fashion.

According to the present invention, the color spectrum of the illuminating light beam, or that of the image of surface 5 of wafer 4 captured by CCD camera 3, is modified by color filter 17 and/or by dichroic coating 16 on the surface of semitransparent mirror 15 in such a way that the color spectrum of the illuminating light beam, or that of the image of surface 5 of wafer 4 captured by CCD camera 3, is better adapted to the spectral sensitivity of CCD camera 3 and its CCD sensors. This makes it possible, in particular, to modulate the color image channels of CCD camera 3 more uniformly. This results in more uniform signal-to-noise ratios in the color image channels of CCD camera 3, so that the color image signals captured from CCD camera 3 can be more consistently and more appropriately processed and evaluated. In particular, one and the same amplifier can be used to amplify all the color image signals, with no need to use different gain factors for the various color image channels.

Color filter 17 and/or dichroic coating 16 can modify the color spectrum of the illuminating light beam, and/or that of the image of surface 5 of wafer 4 captured by CCD camera 3, in such a way that the ratios of the intensities of the color signals of CCD camera 3 are appropriately modified so as to achieve a more uniform modulation of the color image channels of CCD camera 3.

In a preferred embodiment, the intensity of a color image signal of CCD camera 3 in a red spectral region is increased relative to the intensity of a color signal of CCD camera 3 in a blue spectral region, so that the color image channels of CCD camera 3 are substantially uniformly modulated. Because the color spectrum of illumination device 2 is constant, the ratio of the intensities of the color image signals of the CCD camera in the red or blue spectral region to the intensity of the color image signal in the green spectral region is thus also automatically modified.

In the arrangement shown in FIG. 1, a xenon flash lamp is preferably used as light source 10 as illumination device 2. According to the present invention it is preferable to use xenon lamps whose color spectrum in the visible spectral region between 380 and 780 nm very closely matches the spectral profile of a black body having a color temperature of approximately 15,000 K. In order to adapt the spectrum of a xenon flash lamp to the spectral sensitivity of commercially available CCD cameras and to the spectral reflectivity of Si wafers, it is preferable to use a ½ color temperature orange (CTO) filter which changes the color temperature of the incident illuminating light beam of the xenon flash lamp, or of the image of surface 5 of wafer 4 captured by CCD camera 3, to a color temperature of approximately 5600 K.

Light source 10 can, of course, also be a monochromatic or polychromatic light source, as described below by way of example with reference to FIG. 3.

Color filter 17 can be arranged statically in the beam path, in which case the transmittance of color filter 17 in the various spectral regions is defined in advance, for example on the basis of the spectral reflectivity of a reference wafer. The transmittance of color filter 17 can also increase, continuously or in steps, along a spatial direction, so that by spatial displacement of color filter 17 relative to the beam path of the illuminating light beam, or of the light reflected, scattered, or refracted from surface 5 of the wafer, the color spectrum of the illuminating light beam, or of the light reflected, scattered, or refracted from surface 5 of the wafer, can be suitably modified. For example, color filter 17 can be rectangular, and the transmittance can increase along one longitudinal side of color filter 17. Alternatively, color filter 17 can be circular, and the transmittance can increase along the circumferential direction of color filter 17. As indicated by double arrow 30, a color filter 17 of this kind having a locally varying, transmittance can be moved or displaced in the beam path of the illuminating light beam, or of the light reflected, scattered, or refracted from surface 5 of wafer 4, until a position of color filter 17 is found in which the color image channels of CCD camera 3 are more uniformly modulated and an adaptation to the spectral sensitivity of the CCD camera is achieved.

The modulation of the color image channels of CCD camera 3 is ascertained and evaluated using a frame grabber serving as data readout device, and a computer 13. On the basis of the color image signals read out by the computer, the transmittance of color filter 17, 18 and/or 19 can be modified, by automatic movement or displacement thereof, until a suitable transmittance is found at which the color image channels of CCD camera 3 are substantially uniformly modulated, and an adaptation to the spectral sensitivity of CCD camera 3 is achieved.

Figure 2:
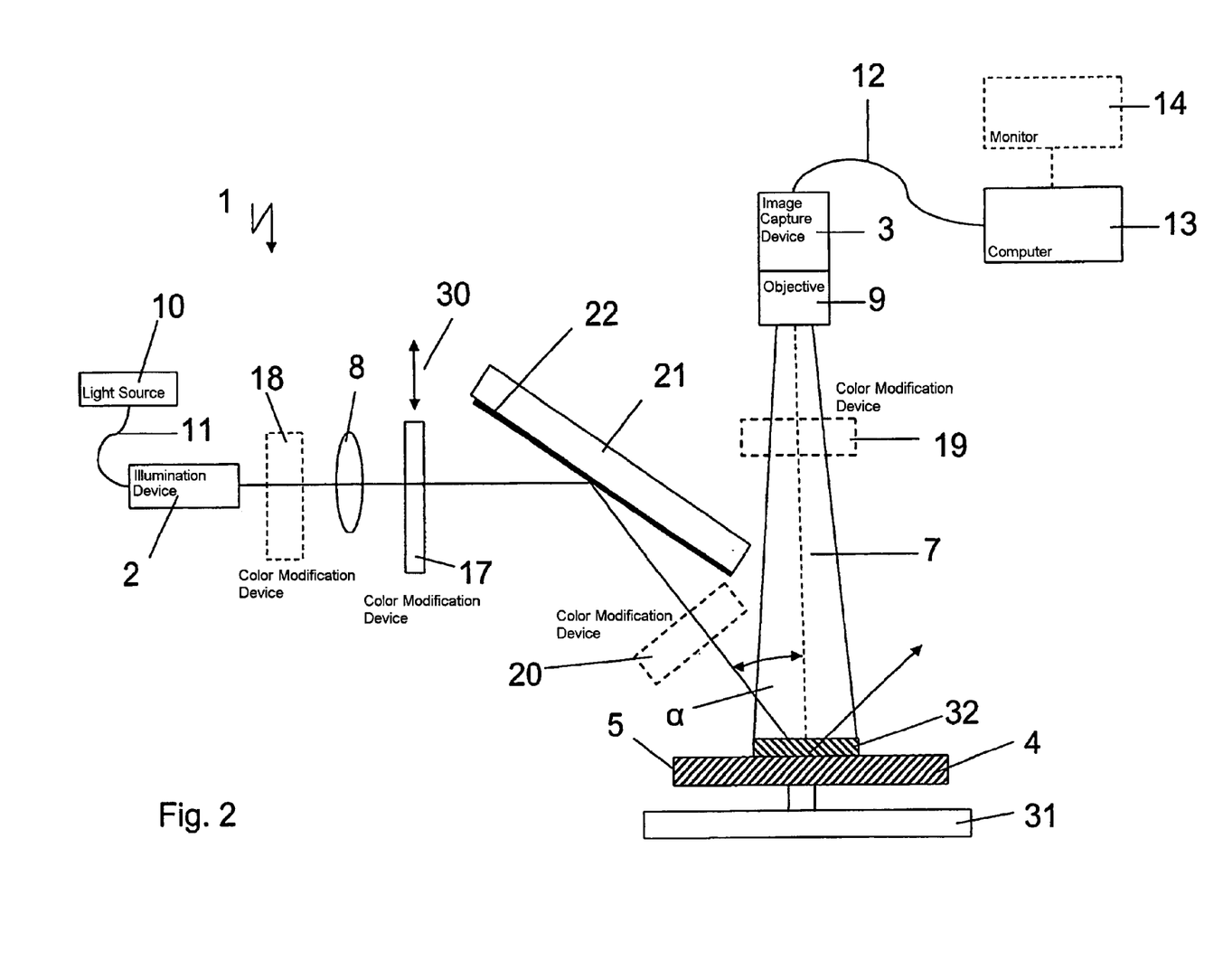
FIG. 2 shows a second embodiment of a wafer inspection apparatus according to the present invention, with detection in a dark-field arrangement.
Figure 3:
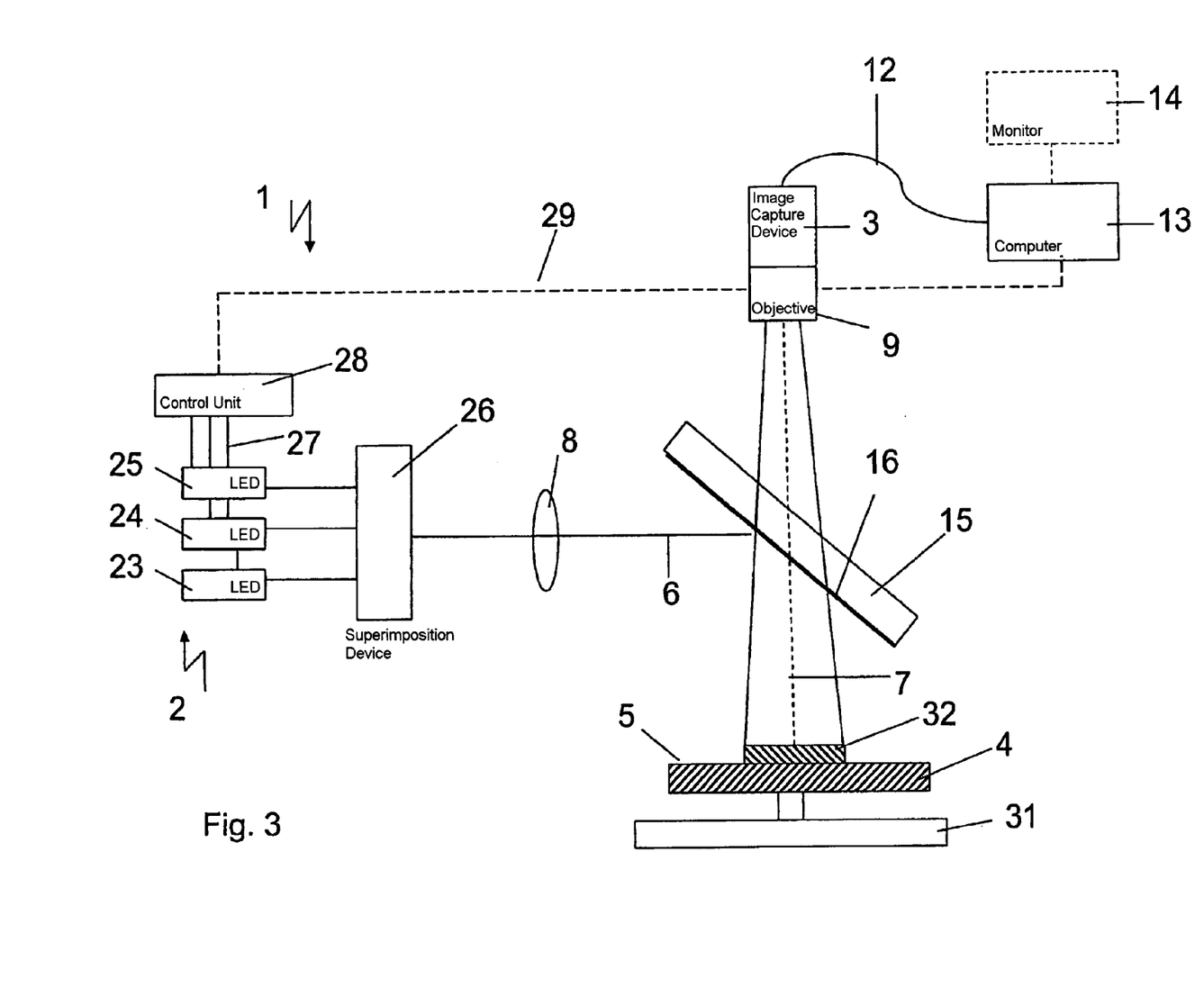
FIG. 3 shows a third embodiment of a wafer inspection apparatus according to the present invention, with detection in a bright-field arrangement.
Figure 4:
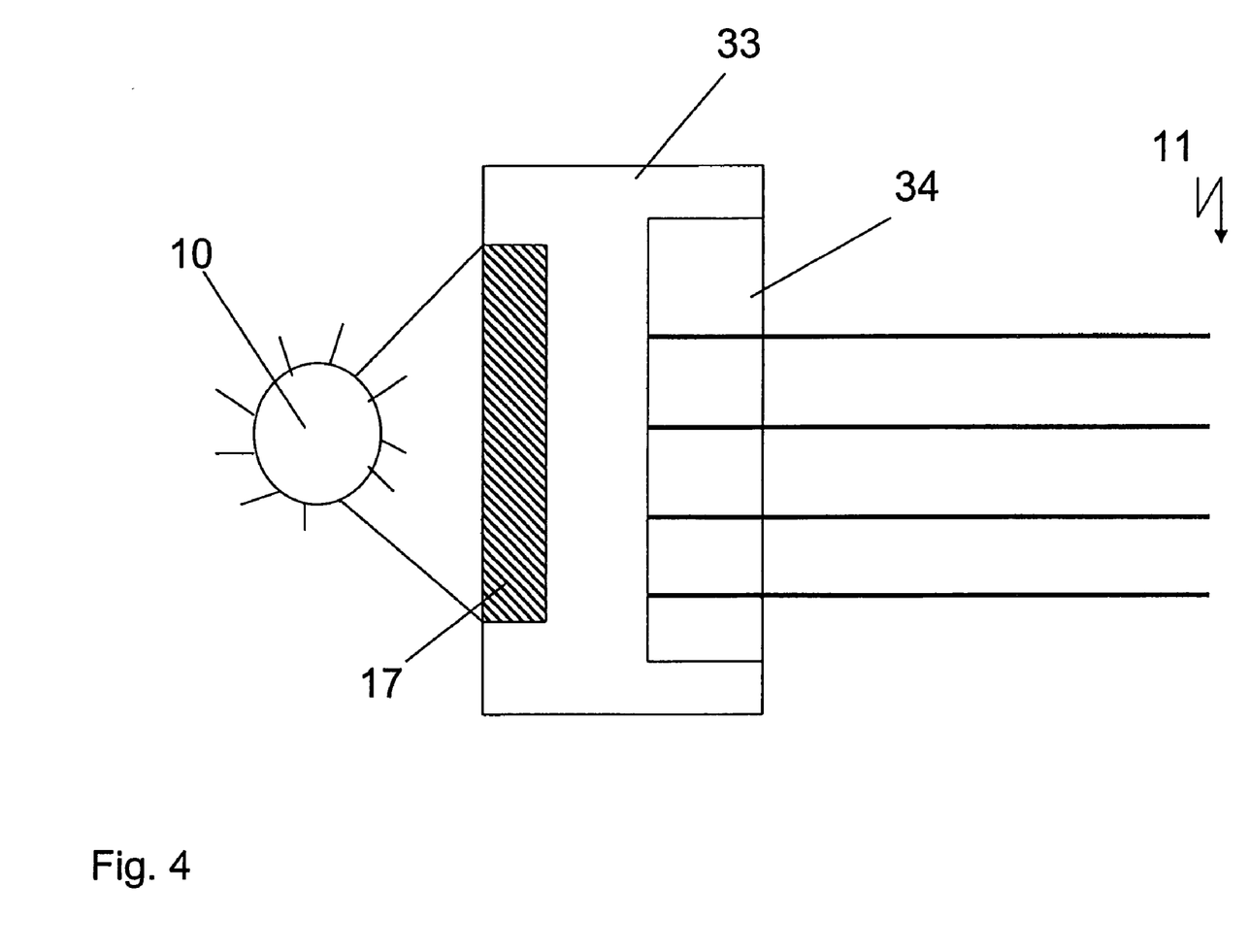
FIG. 4 shows, in an enlarged view, the coupling of light from a light source into a light guide bundle, as applicable in the context of the first through third embodiments.

FIG. 4 shows, in an enlarged view, the coupling of light of a light source 10 into a light guide bundle 11, as applicable in the context of the embodiments shown in FIGS. 1 through 3. Light source 10 can be a thermal radiator, an LED or linear LED arrangement, or a laser diode or linear laser diode arrangement. The light radiated from light source 10 is coupled into the light guides of light guide bundle 11. The ends of the light guides are received in a receptacle 34 that is held in mechanically stable fashion in a holder 33. Located at the front end of holder 33, in the beam path between light source 10 and the fiber ends of light guide bundle 11, is a color filter 17 serving as color modification device. Although not depicted, further optical elements, for example an incoupling optical system, lenses, or a diffusion disk for homogenizing the illuminating light beam, can also be arranged in the beam path between light source 10 and light guide bundle 11. The fiber-optic system thus constituted can also be embodied as a large-area fiber radiator.

As FIG. 1 shows, wafer 4 is held statically or rotatably on a wafer receiving device 31. The orientation of wafer 4 on wafer receiving device 31 can be ascertained by detecting a marking provided on the circumferential edge of wafer 4, for example a wafer notch or a flat. Wafer inspection apparatus 1 can also have associated with it a prealigner (not depicted) that transfers wafer 4 to wafer receiving device 31 in a definable alignment. The location of macrodefects on surface 5 of wafer 4 can thus, according to the present invention, also be detected in positionally resolved fashion.

FIG. 2 shows a second embodiment of a wafer inspection apparatus 1 according to the present invention, with detection in a dark-field arrangement. As FIG. 2 shows, the light beam radiated from illumination device 2 is deflected by means of a mirror 21 and is incident at an incidence angle $\alpha$ (alpha) onto surface 5 of wafer 4. The illuminating light beam reflected from illuminated region 32 is not imaged into CCD camera 3. Instead, only scattered light or diffracted light, which can also derive e.g. from macrodefects on surface 5 of wafer 4 in illuminated region 32, is imaged into CCD camera 3.

As FIG. 2 shows, a color filter 17 serving as color modification device, which modifies the color spectrum of the illuminating light beam, is arranged in the beam path of the illuminating light beam after imaging optical system 8. As indicated by dashed lines 18, 19, and 20 in FIG. 2, color filter 17 can also be arranged in front of imaging optical system 8, between mirror 21 and surface 5 of wafer 4, or in the beam path between surface 5 of wafer 4 and CCD camera 3. A dichroic coating can also be provided, in the manner described in conjunction with FIG. 1, on surface 22 of mirror 21 in order to modify the color spectrum of the incident illuminating light beam upon reflection at mirror 21.

The incidence angle $\alpha$ (alpha) can, of course, also be modified with the aid of an alpha adjusting mechanism (not depicted). As depicted in FIGS. 1 and 2, imaging axis 7 of CCD camera 7 is substantially perpendicular to surface 5 of wafer 4. Advantageously, the image field of CCD camera 3 substantially completely overlaps illuminated region 32 on surface 5 of wafer 4.

As shown in FIGS. 1 and 2, illumination axis 6 and the normal line onto surface 5 of wafer 4 span a plane in which imaging axis 7 lies. Although this arrangement is particularly useful for aligning wafer inspection apparatus 1, CCD camera 3 can, of course, also be pivoted out of the drawing plane of FIGS. 1 and 2 in such a way that imaging axis 7 no longer lies in the plane spanned by illumination axis 6 and the normal line onto surface 5 of wafer 4.

FIG. 3 shows a further embodiment of a wafer inspection apparatus 1 according to the present invention, with detection in a bright-field arrangement. As shown in FIG. 3, illumination device 2 encompasses three LEDs 23 through 25 that radiate illuminating light beams in three different spectral regions, preferably in a red, green, and blue spectral region. The illuminating light beams radiated by LEDs 23 through 25 are superimposed in beam superimposition device 26, for example a prism arrangement, and then imaged onto surface 5 of wafer 4 in the manner described in conjunction with FIG. 1.

LEDs 23 through 25 are connected via connecting lines 27 to a control unit 28 that activates LEDs 23 through 25. By modifying the LED driver current, the intensity of a particular LED 23 through 25 can be suitably adjusted and almost arbitrarily increased or reduced. The characteristic curves of the LEDs can be stored in a memory (not depicted) of control unit 28.

As indicated by the dashed line, control unit 28 is connected via a data connection line 29 to a computer 13, serving as data readout device, that reads out and evaluates the color image signals of CCD camera 3. From the color image signals, computer 13 can generate control signals that are inputted into control unit 28 in order to adjust the intensities of the illuminating light beams radiated by LEDs 23 through 25 individually in such a way that an adaptation of the color spectrum of the illuminating light beams, or of the image of surface 5 of wafer 4 captured by CCD camera 3, can be achieved, and the color image channels of CCD camera 3 can be modulated substantially uniformly. The individual adaptation of the intensities of the illuminating light beams radiated by LEDs 23 through 25 can also be accomplished in advance on the basis of a reference wafer having a defined reflectivity.

Computer 13 and control unit 28 can also constitute a control loop in order to regulate the intensities of the illuminating light beams radiated by LEDs 23 through 25 in such a way that the color image channels of CCD camera 3 are modulated substantially uniformly.

Although the use of LEDs has been described in conjunction with FIG. 3, other emitters can also be used as color light sources 23 through 25, for example lasers or light-emitting plastics that emit in different spectral regions. A dark-field arrangement as described in conjunction with FIG. 2 can, of course, also be used with the wafer inspection apparatus according to FIG. 3.

Figure 5A:
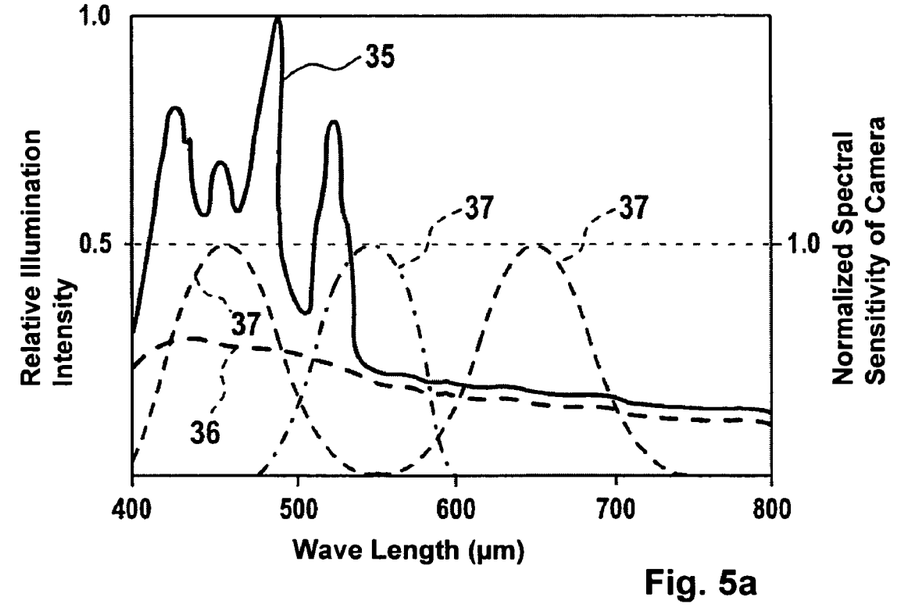
FIG. 5a is a schematic depiction of the spectral sensitivity of a CCD camera and the spectral distribution of a thermal radiator, before and after a modification of the color spectrum according to the present invention.

FIG. 5a is a schematic depiction of the spectral sensitivity of a CCD camera and the spectral distribution of a thermal radiator before and after a modification of the color spectrum according to the present invention. The approximately Gaussian curves labeled with reference characters 37 designate the spectral sensitivity of CCD color image sensors in the blue, green, and red spectral regions. As shown in FIG. 5a, the CCD color image sensors have approximately the same spectral sensitivity in the exemplary embodiment depicted.

The curve labeled with reference character 35 designates the spectrum of a xenon flash lamp in the visible spectral region between 400 nm and 800 nm. Lastly, the curve labeled with reference character 36 designates the spectrum of the xenon flash lamp after a color filter, serving as color modification device, has been introduced into the beam path of the illuminating light beam. As depicted in FIG. 5a, the color filter attenuates the illuminating light beam in the blue spectral region, while the illuminating light beam is not substantially attenuated in the other visible spectral regions. A substantially more uniform spectral distribution of the illuminating light beam can thereby be obtained.

Figure 5B:
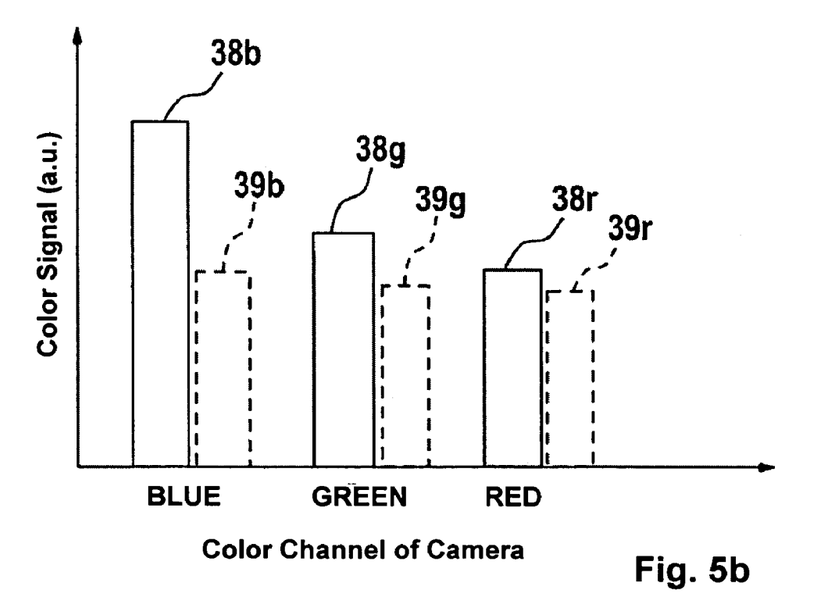
FIG. 5b shows the intensities of color image signals of the CCD camera before and after a modification of the color spectrum according to the present invention.

FIG. 5b shows the intensities of color image signals of the CCD camera before and after a modification of the color spectrum according to the present invention. Bars 38b, 38g, and 38r depicted with solid lines designate the intensities of the color image signals in the blue, green, and red spectral regions for an illuminating light beam having the spectral distribution of curve 35 according to FIG. 5a. Bars 39b, 39g, and 39r depicted with dashed lines designate the intensities of the color image signals in the blue, green, and red spectral regions for an illuminating light beam having the spectral distribution of curve 36 according to FIG. 5a, after a color filter serving as color modification device has been introduced into the beam path of the illuminating light beam.

As shown in FIG. 5b, the intensity of the red color image signal remains almost unchanged. The intensities of the green and blue colors signals, however, are attenuated relative to the intensity of the red color image signal. After introduction of the color filter, the intensities of the color image signals are substantially equally distributed.

As will be apparent to one skilled in this art upon examination of the description above, the wafer inspection apparatus according to the present invention can be controlled by a program that executes on a computer or another suitable data processing device, for example on a microprocessor. The program can be stored on a data medium, for example a diskette, a magnetic or optical disk, or a non-volatile memory module, in order to be loaded into the working memory of the data processing device to carry out the method according to the present invention.

The wafer inspection apparatus according to the present invention is suitable for the detection of macrodefects of many different types, for example particles, protrusions, depressions, or distortions on the surface of wafers. From the color distribution of the reflected or scattered light that is detected, it is also possible to draw conclusions as to irregularities in the surface coating of wafers, for example dielectric coatings, metallizations, or photoresist layers.

What is claimed is:

1. An apparatus for inspection of a wafer comprising:
    at least one illumination device that radiates an illuminating light beam onto a surface of the wafer,
    an image capture device that has a predefined spectral sensitivity and captures an image of an illuminated region on the surface of the wafer in a plurality of spectral regions, and
    a color modification device for modifying the color spectrum of the illuminating light beam or that of the image that is acquired of the surface of the wafer,
    wherein the color modification device is designed in such a way that the color spectrum of the illuminating light beam, or that of the image that is acquired of the surface of the wafer, is adaptable to the spectral sensitivity of the image capture device.

2. The apparatus as defined in claim 1, wherein in order to adapt the color spectrum of the illuminating light beam, or that of the image that is acquired of the surface of the wafer, to the spectral sensitivity of the image capture device an intensity of a color image signal of the image capture device in one spectral region is modifiable by modifying the color spectrum of the illuminating light beam, or that of the image that is acquired of the surface of the wafer, relative to an intensity of a different color image signal of the image capture device in a different spectral region.

3. The apparatus as defined in claim 1, in which the color modification device is designed in such a way that an intensity of a color image signal in a red spectral region is modifiable by modifying the color spectrum of the illuminating light beam, or that of the image that is acquired of the surface of the wafer, relative to an intensity of a color image signal in a blue spectral region.

4. The apparatus as defined in claim 1, wherein the color modification device comprises at least one color filter device in order to modify the color spectrum of the illuminating light beam.

5. The apparatus as defined in claim 4, wherein the color filter device comprises at least one color filter that is arranged in a beam path of the illuminating light beam.

6. The apparatus as defined in claim 5, in which a transmittance of the color filter is continuously modifiable.

7. The apparatus as defined in claim 4, wherein the color filter device comprises at least one color filter that is arranged between an illumination light source and a fiber end of a light guide or of a light guide bundle.

8. The apparatus as defined in claim 4, wherein the color filter device comprises a CTO filter in order to change a color temperature of the illuminating light beam to approximately 5600 K.

9. The apparatus as defined in claim 1, wherein the illumination device comprises a thermal radiator.

10. The apparatus as defined in claim 1, wherein the illumination device comprises a xenon flash lamp.

11. The apparatus as defined in claim 1, wherein the illumination device comprises at least three color light sources that radiate illuminating light beams each having a different color spectrum.

12. The apparatus as defined in claim 11, further comprising a control unit for modifying an intensity of at least one color light source.

13. The apparatus as defined in claim 12, wherein the control unit regulates the intensity of the at least one color light source in such a way that the image capture device is modulated uniformly in all color image channels.

14. The apparatus as defined in claim 1, further comprising a data readout device for reading out color image signals of the image capture device and evaluating the color image signals in the plurality of spectral regions.

15. The apparatus as defined in claim 14, further comprising:
 a control unit for modifying an intensity of at least one color light source, and
 a data connection that connects the control unit to the data readout device, the control unit regulating the intensity of at least one color light source to a definable intensity.

16. A method for inspection of a wafer, comprising the steps of:
 radiating an illuminating light beam of at least one illumination device onto a surface of the wafer,
 capturing an image of an illuminated region on the surface of the wafer by an image capture device, wherein the image capture device has a predefined spectral sensitivity in a plurality of spectral regions,
 modifying the color spectrum of the illuminating light beam, or that of the image that is acquired of the surface of the wafer, and
 carrying out the modification such that the color spectrum of the illuminating light beam, or that of the image that is acquired of the surface of the wafer, is adapted to the spectral sensitivity of the image capture device.

17. The method as defined in claim 16, wherein for adaptation of the color spectrum of the illuminating light beam, or that of the image that is acquired of the surface of the wafer, to the spectral sensitivity of the image capture device, an intensity of a color image signal of the image capture device in one spectral region is modified relative to an intensity of a different color image signal of the image capture device in a different spectral region.

18. The method as defined in claim 16, wherein the intensity of a color image signal in a red spectral region is modified by modifying the color spectrum of the illuminating light beam, or that of the image that is acquired of the surface of the wafer, relative to the intensity of a color image signal in a blue spectral region.

19. The method as defined in claim 16, wherein at least one color filter is arranged in a beam path of the illuminating light beam.

20. The method as defined in claim 19, wherein a transmittance of the color filter is continuously modified.

21. The method as defined in claim 16, wherein at least three illuminating light beams are radiated, each in different spectral regions.

22. The method as defined in claim 16, wherein a control unit regulates an intensity of at least one illuminating light beam to a definable intensity, so that the image capture device is uniformly modulated in all color image channels.

23. A computer program, wherein the computer program carries out the method as defined in claim 16 upon execution on a computer.

24. A computer program comprising a program code to carry out all the steps according to claim 16 when the program is executed on a computer.

* * * * *